(12) United States Patent
Corminboeuf et al.

(10) Patent No.: US 9,533,964 B2
(45) Date of Patent: Jan. 3, 2017

(54) PIPERAZINE SUBSTITUTED BRIDGED SPIRO[2.4]HEPTANE DERIVATIVES AS ALX RECEPTOR AGONISTS

(71) Applicant: Actelion Pharmaceuticals Ltd, Allschwil (CH)

(72) Inventors: Olivier Corminboeuf, Allschwil (CH); Sylvaine Cren, Allschwil (CH); Davide Pozzi, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/905,768

(22) PCT Filed: Jul. 17, 2014

(86) PCT No.: PCT/EP2014/065351
§ 371 (c)(1),
(2) Date: Jan. 15, 2016

(87) PCT Pub. No.: WO2015/007830
PCT Pub. Date: Jan. 22, 2015

(65) Prior Publication Data
US 2016/0152584 A1    Jun. 2, 2016

(30) Foreign Application Priority Data

Jul. 18, 2013   (WO) .................. PCT/IB2013/055906

(51) Int. Cl.
*C07D 295/13* (2006.01)
*C07D 295/14* (2006.01)

(52) U.S. Cl.
CPC ........... *C07D 295/13* (2013.01); *C07D 295/14* (2013.01)

(58) Field of Classification Search
None
See application file for complete search history.

(56) References Cited

U.S. PATENT DOCUMENTS

2003/0147883 A1   8/2003   Wang et al.

FOREIGN PATENT DOCUMENTS

| WO | WO 95/02587 A1 | 1/1995 |
|----|----|----|
| WO | WO 03/082314 A2 | 10/2003 |
| WO | WO 2005/047899 A2 | 5/2005 |
| WO | WO 2009/077954 A1 | 6/2009 |
| WO | WO 2009/077990 A1 | 6/2009 |
| WO | 2010134014 * | 11/2010 |
| WO | WO 2010/134014 A1 | 11/2010 |
| WO | WO 2010/143116 A1 | 12/2010 |
| WO | WO 2010/143158 A1 | 12/2010 |
| WO | WO 2011/163502 A1 | 12/2011 |
| WO | WO 2012/066488 A2 | 5/2012 |
| WO | WO 2012/077049 A1 | 6/2012 |
| WO | WO 2012/077051 A1 | 6/2012 |
| WO | WO 2013/009543 A1 | 1/2013 |
| WO | WO 2013/171687 A1 | 11/2013 |
| WO | WO 2013/171694 A1 | 11/2013 |
| WO | WO 2014/138037 A1 | 9/2014 |
| WO | WO 2014/138046 A1 | 9/2014 |
| WO | WO 2015/007830 A1 | 1/2015 |
| WO | WO 2015/019325 A1 | 2/2015 |

OTHER PUBLICATIONS

Bannenberg, "Anti-Inflammatory Actions of Lipoxins", Expert Opinion on Therapeutic Patent, 17(6), 591-605, 2007.
Burli et al., "Potent hFPRL1 (ALXR) Agonists as Potential Anti-Inflammatory Agents", Bioorganic & Medicinal Chemistry Letters, 16(4), 3713-3718, 2006.
Celik et al., "Lipoxin A4 Levels in Asthma: Relation with Disease Severity and Aspirin Sensitivity", Clinical and Experimental Allergy, 37, 1494-1501, 2007.
Chiang et al., "The Lipoxin Receptor ALX: Potent Ligand-Specific and Stereoselective Actions in Vivo", Pharmacology and Reviews, 58, 463-487, 2006.
Edwards et al., "Integration of Virtual Screening with High-Throughput Flow Cytometry to Identify Novel Small Molecule Formylpeptide Receptor Antagonists", Molecular Pharmacology, 68, 2005.
Gewirtz et al., "Mechanisms of Active Intestinal Inflammation and Potential Down-Regulation Via Lipoxins", Adv Exp Med Biol, 507, 229-36, 2002.
Gronert et al., "A Role for the Mouse 12/15-Lipoxygenase Pathway in Promoting Epithelial Wound Healing and Host Defense", The Journal of Biological Chemistry, 280, 15267-15278, 2005.
Gronert, "Lipoxins in the Eye and Their Role in Wound Healing", Prostaglandins Leukot Essent Fatty Acids, 73, 221-229, 2005.
Jin et al., "Posttreatment with Aspirin-Triggered Lipoxin A4 Analog Attenuates Lipopolysaccharide-Induced Acute Lung Injury in Mice: The Role of Heme Oxygenase-1", Anesth Analg 104, 369-377, 2007.

(Continued)

*Primary Examiner* — Karl J Puttlitz
(74) *Attorney, Agent, or Firm* — Arent Fox LLP

(57) ABSTRACT

The present invention relates to a piperazine substituted bridged spiro[2.4]heptane derivative of formula (I),

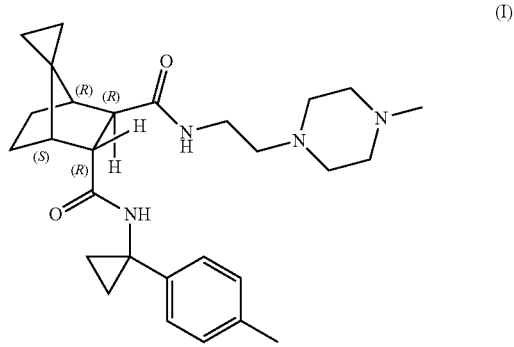

its preparation and its use as pharmaceutically active compound.

5 Claims, No Drawings

(56) References Cited

OTHER PUBLICATIONS

Karp et al., "Defective Lipoxin-Medicated Anti-inflammatory Activity in the Cystic Fibrosis Airway" Nature Immunology, 5, 388-392. 2004.
Le et al., "Biologically Active Peptides Interacting with the G Protein-Coupled Formylpeptide Receptors", Protein & Peptide Letters, 14, 846-853, 2007.
Levy et al., "Lipoxin A4 Stable Analogs Reduce Allergic Airway Responses via Mechanisms Distinct from CysLT1 Receptor Antagonism", FASEB Journal, 21, 3877-3884, 2007.
Levy et al., "Multi-Pronged Inhibition of Airway Hyper-Responsiveness and Inflammation by Lipoxin A4", Nature Medicine, 8, 1018-1023, 2002.
Mamiya et al., "[Gly14]-Humanin Improved the Learning and Memory Impairment Induced by Scopolamine in Vivo", British Journal of Pharmacology, 134, 1597-1599, 2001.
Miao et al., "S14G-Humanin Ameliorates AB25-35-Induced Behavioral Deficits by Reducing Neuroinflammatory Responses and Apoptosis in Mice", Neuropeptides, 42, 557-567, 2008.
Planaguma et al, "Airway LXA4 Generation and LXA4 Receptor Expression Are Decreased in Severe Asthma", Am J Respir Crit Care Med, 178, 574-582, 2008.
Remington, The Science and Practice of Pharmacy, 21st Edition.
Schwab et al, "Lipoxins and New Lipid Mediators in the Resolution of Inflammation", Current Opinion in Pharmacology, 414-420, 2006.
Sodin-Semrl et al, "Lipoxin A4 Counteracts Synergistic Activation of Human Fibroblast-Like Synoviocytes", International Journal of Immunopathology and Pharmacology, 17, 15-25, 2004.
Stahl et al., "Handbook of Pharmaceutical Salts. Properties, Selection and Use", 2008.
Wouters et al, "Pharmaceutical Salts and Co-crystals", Royal Society of Chemistry, 2012.
Yazawa et al., "Amyloid Peptide (AB42) is Internalized via the G-Protein-Couplea Receptor FPRL1 and Forms Fibrillar Aggregates in Macrophages1", FASEB Journal, 15, 2454-2462, 2001.
Ying et al., Humanin, a Newly Identified Neuroprotective Factor, Uses the G Protein-Coupled Forrnylpeptide Receptor-Like-1 as a Functional Receptor, The Journal of Immunology, 172, 7078-7085, 2004.
Zhang et al., "BML-111, a Lipoxin Receptor Agonist, Modulates the Immune Response and Reduces the Severity of Collagen-Induced Arthritis", Inflammation Research, 57, 157-162, 2008.
International Search Report of PCT/EP2014/065351 dated Oct. 2, 2014.
Martins et al., ATLa, an Aspirin-Triggered Lipoxin A4 Synthetic Analog, Prevents the Inflammatory and Fibrotic Effects of Bleomycin-Induced Pulmonary Fibrosis, The Journal of Immunology, 2009, pp. 5374-5381, vol. 182.
Schottelius et al., "An Aspirin-Triggered Lipoxin A4 Stable Analog Displays a Unique Topical Anti-Inflammatory Profile," The Journal of Immunology, 2002, pp. 7063-7070, vol. 169.

\* cited by examiner

PIPERAZINE SUBSTITUTED BRIDGED SPIRO[2.4]HEPTANE DERIVATIVES AS ALX RECEPTOR AGONISTS

CROSS-REFERENCE TO RELATED APPLICATIONS

This application is a National Stage entry of International Application No. PCT/EP2014/065351, filed Jul. 17, 2014, which claims priority to International Application No. PCT/IB2013/055906, filed Jul. 18, 2013. The disclosures of the prior applications are hereby incorporated in their entirety by reference.

The present invention relates to a piperazine substituted bridged spiro[2.4]heptane derivative of formula (I) and its use as pharmaceutical. The invention also concerns related aspects including processes for the preparation of the compound, pharmaceutical compositions containing the compound of formula (I), and especially its use as ALX receptor (ALXR) agonists.

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogues, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). Lipoxin A4 inhibited IL-6 expression in human fibroblast-like synoviocytes (Sodin-Semrl et al, Int J Immunopathol Pharmacol (2004) 17:15-25) and a stable FPR2 agonist, BML-111, reduced the severity of collagen-induced arthritis (Zhang et al., (2008) Inflamm Res 57:157-162) demonstrating a possible use of FPR2 agonists in the treatment of rheumatoid arthritis. Mice with acute lung injury (ALI) showed reduced pulmonary inflammation when treated with stable lipoxin A4 (Jin et al., (2007) Anesth Analg 104:369-377). Lower lipoxin A4 levels in severe asthma (Celik et al., (2007) Clin Exp Allergy 37:1494-1501; Planaguma et al, (2008) Am J Respir Crit Care Med 178:574-582) and improvement of asthma responses in animal models by stable lipoxin A4 analogs (Levy et al., (2002) Nat Med 8:1018-1023; Levy et al., (2007) FASEB J 21:3877-3884) have been described. In cystic fibrosis it was shown, that the levels of pulmonary lipoxin A4 are decreased both in the lung of cystic fibrosis patients and in animal models of the disease (Karp et al., (2004) Nat Immunol 5:388-392); treatment with a stable lipoxin analog improved inflammatory cell accumulation within the diseased lung and reduced body weight loss in the same animals (Karp et al., (2004) Nat Immunol 5:388-392). Topical treatment with lipoxin A4 increases re-epithelization and decreases inflammation of the dry corneal surface (Gronert, (2005) Prostaglandins Leukot Essent Fatty Acids 73:221-229; Gronert et al., (2005) J Biol Chem 280:15267-15278) demonstrating a possible use of FPR2 agonists in the treatment of keratoconjunctivitis sicca. Oral administration of lipoxin A4 analogs reduced the severity of colitis in a mouse model of inflammatory bowel disease (Gewirtz et al., (2002) Eicosanoids and other Bioactive Lipids in Cancer, Inflammation, and Radiation Injury, Kluwer Academic/Plenum Publishers, 229-236). ALXR was also identified as a functional receptor of a various number of peptides, including a fragment of the prion protein, a peptide derived from gp120 of the Human Immunodeficiency Virus (HIV)-1$_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. Further, humanin is a high-affinity ligand for ALXR and is neuroprotective in models of Alzheimer's Disease (Mamiya et al., (2001) Br J Pharmacol 134:1597-1599; Ying et al., (2004) J Immunol 172:7078-7085; Miao et al., (2008) Neuropeptides 42:557-567).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides a piperazine substituted bridged spiro[2.4]heptane derivative, which is a non-peptide agonist of human ALX receptor. Other bridged spiro[2.4] heptane derivatives with agonistic activity on human ALX receptor have been disclosed in WO 2010/134014, WO2011/163502, WO2012/066488, WO2013/009543, WO2013/171694 and WO2013/171687. Different bridged spiro[2.4]heptane derivatives have been disclosed in WO95/02587. The compound is useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition it is useful for the prevention or treatment of autoimmune diseases and for the modulation of immune responses (especially those elicited by vaccination).

The compound of the present invention shows a high stability in human plasma.

1) The present invention relates to a compound of formula (I), which compound is (5R)—N$^5$-(1-(p-tolypcyclopropyl)-(6R)—N$^6$-(2-(4-methylpiperazin-1-yl)ethyl)-(4S,7R)-[4,7-ethylene-spiro[2.4]heptane]-5,6-dicarboxamide;

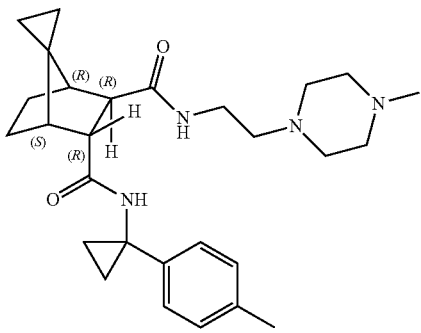

and to the salts (in particular pharmaceutically acceptable salts) of such a compound.

The present invention also includes isotopically labelled, especially $^2$H (deuterium) labelled compounds of formula (I), which compounds are identical to the compound of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compound of formula (I) is not isotopically labelled, or is labelled only with one or more deuterium atoms. In a sub-embodiment, the compound of formula (I) is not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

Where the plural form is used for compounds, salts, pharmaceutical compositions, diseases and the like, this is intended to mean also a single compound, salt, pharmaceutical composition, disease or the like.

The compound of formula (I) according to embodiment 1), or a pharmaceutically acceptable salt thereof, is suitable for use as a medicament. In particular, the compound of formula (I) modulates the ALX receptor, i.e. it acts as a ALX receptor agonists, and is useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases, leukemias and amyloid-mediated disorders (especially Alzheimer's disease); in addition the compound is useful for the modulation of immune responses (especially those elicited by vaccination).

In particular, the compound of formula (I) according to embodiment 1), or a pharmaceutically acceptable salt thereof, is suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) In a further embodiment the compound of formula (I) according to embodiments 1), or a pharmaceutically acceptable salt thereof, is particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include gingivitis, periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, dicoid lupus and epidermolysis.

5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behçet syndrome uveitis, conjunctivitis, keratoconjunctivitis sicca, Sjögren syndrome keratoconjunctivitis sicca, and vernal conjunctivitis; diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, giant cell arteritis, neutrophilic dermatoses, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.

5d) Further inflammatory diseases in which autoimmune reactions are implicated or which have an autoimmune component or aetiology include rheumatoid arthritis, Hashimoto's thyroid and diabetes type I or II.

Further, the compound of formula (I) according to embodiment 1), or a pharmaceutically acceptable salt thereof, is suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e.g. pancreatic islet cells.

Further, the compound of formula (I) according to embodiment 1), or a pharmaceutically acceptable salt thereof, is suitable for the prevention or treatment of HIV-mediated retroviral infections. HIV-mediated retroviral infections include, but are not limited to, one, several or all of the groups of diseases and disorders caused by HIV-1 and HIV-2 strains such as GUN-4v, GUN-7 wt, AG204, AG206, AG208, HCM305, HCM308, HCM342, mSTD104, and HCM309.

Further, the compound of formula (I) according to embodiment 1), or a pharmaceutically acceptable salt thereof, is suitable for the prevention or treatment of cardiovascular disorders. Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compound of formula (I) according to embodiment 1), or a pharmaceutically acceptable salt thereof, is suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compound of formula (I) according to embodiment 1), or a pharmaceutically acceptable salt thereof, is suitable for the prevention or treatment of neurological disorders. In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea.

Further, the compound of formula (I) according to embodiment 1), or a pharmaceutically acceptable salt thereof, is suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compound of formula (I) according to embodiment 1), or a pharmaceutically acceptable salt thereof, is suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compound of formula (I) according to embodiment 1), or a pharmaceutically acceptable salt thereof, is suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis.

Further, the compound of formula (I) according to embodiment 1), or a pharmaceutically acceptable salt thereof, is suitable for the modulation of immune responses. The modulation of immune responses includes, but is not limited to, methods based on the administration to a subject a composition of at least one antigen and the compound of formula (I) according to embodiment 1), or a pharmaceutically acceptable salt thereof. In some cases, the antigen-containing composition is administrated first, followed by administration of the composition of the compound of formula (I) according to embodiment 1), or a pharmaceutically acceptable salt thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of the compound of formula (I) according to embodiment 1), or a pharmaceutically acceptable salt thereof, and the antigen, as compared to sole administration of the antigen;

2) A greater sensitivity to small amounts of antigen (e.g., toxin or pathogen) or antigens that do not habitually induce strong immune responses; and 3) More effective anti-tumor therapies.

Further, the compound of formula (I) according to embodiment 1), or a pharmaceutically acceptable salt thereof, is suitable for the prevention or treatment of cystic fibrosis, pulmonary fibrosis, pulmonary hypertension, wound healing, diabetic nephropathy, reduction of inflammation in transplanted tissue, and inflammatory diseases caused by pathogenic organisms.

Especially, the compound of formula (I) according to embodiment 1), or a pharmaceutically acceptable salt thereof, is suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection;

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;

3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);

4) HIV-mediated retroviral infections such as diseases and disorders caused by HIV-1 and HIV-2 strains such as GUN-4v, GUN-7 wt, AG204, AG206, AG208, HCM305, HCM308, HCM342, mSTD104, and HCM309;

5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid β deposition of amyloid plaques;

6) Neurological disorders such as stroke, cerebral ischemia, Alzheimer's disease, and Parkinson's disease;

7) Prion-mediated diseases, also known as transmissible spongiform encephalopathies (TSEs), such as kuru, Gerstmann-Sträussler-Scheinker syndrome (GSS), Fatal Familial Insomnia (FFI) and Creutzfeldt-Jakob Disease (CJD);

8) Amyloid-mediated disorders;

9) Cystic fibrosis, wound healing and inflammatory diseases caused by pathogenic organisms.

Most preferably, the compound of formula (I) according to embodiment 1), or a pharmaceutically acceptable salt thereof, is suitable for the prevention or treatment of diseases selected from the group consisting of acute lung injury (ALI); asthma; cystic fibrosis; keratoconjunctivitis sicca; inflammatory bowel disease; rheumatoid arthritis; and Alzheimer's Disease.

The invention also relates to the use of the compound of formula (I) according to embodiment 1) for the preparation of pharmaceutical compositions for the treatment and/or prophylaxis of the above-mentioned diseases.

The present invention also relates to pharmaceutically acceptable salts and to pharmaceutical compositions and formulations of the compound of formula (I) according to embodiment 1).

A pharmaceutical composition according to the present invention contains the compound of formula (I) according to embodiment 1) (or a pharmaceutically acceptable salt thereof) as the active agent and optionally carriers and/or diluents and/or adjuvants.

The compound of formula (I) according to embodiment 1) and its pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compound of formula (I) or its pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of the compound of formula (I) according to embodiment 1), or a pharmaceutically acceptable salt thereof.

Any reference to the compound of formula (I) in this text is to be understood as referring also to the salts (and especially the pharmaceutically acceptable salts) of the compound, as appropriate and expedient. The preferences indicated for the compound of formula (I) of course apply mutatis mutandis to the salts and pharmaceutically acceptable salts of the compound of formula (I). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compound of formula (I) can be manufactured by the methods given in the Examples or by analogous methods. Optimum reaction conditions may vary with the particular reactants or solvents used, but such conditions can be determined by a person skilled in the art by routine optimisation procedures.

EXPERIMENTAL PART

Abbreviations (as Used Herein and in the Description Above)

aq. aqueous
bp boiling point
ca. circa
COAD chronic obstructive airway disease
COLD chronic obstructive lung disease
COPD chronic obstructive pulmonary disease
DAD diode array detector
DIPEA diisopropylethylamine
DMEM dulbecco's modified eagle's medium
DMF dimethylformamide
DMSO dimethylsulfoxide
EA ethyl acetate
$EC_{50}$ half maximal effective concentration
EDC N-(3-dimethylaminopropyl)-N'-ethyl-carbodiimide
ELSD evaporative light-scattering detection
Et ethyl
Ether or $Et_2O$ diethylether
FC flash column chromatography on silica gel
FLIPR fluorescence imaging plate reader
FPRL1 formyl-peptide receptor like-1
FPR2 formyl-peptide receptor 2
GSH Glutathione
h hour(s)
HEPES 4-(2-hydroxyethyl)-1-piperazineethanesulfonic acid
hept heptane
HIV human immunodeficiency virus
HOBt hydroxybenzotriazole
HPLC high performance liquid chromatography
LC-MS liquid chromatography-mass spectrometry
lem emission wavelength
lex excitation wavelength
Me methyl
MeOH methanol
min minute(s)
mM millimolar
MS mass spectrometry
nm nanometer
nM nanomolar
NMR nuclear magnetic resonance
org. organic
p para
rf retention factor
rpm rotation per minute
rt room temperature
sat. saturated
TFA trifluoroacetic acid
THF tetrahydrofuran
TLC thin layer chromatography
TMS trimethyl-silyl
$t_R$ retention time
UV ultra violet
Vis visible I Chemistry General. All temperatures are stated in degrees Celsius (° C.). Unless otherwise indicated, the reactions take place at rt.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm): elution with EA, $Et_2O$, hept, hexane, petroleum ether, $CH_2Cl_2$, $CHCl_3$, MeOH, $NH_4OH$ or mixtures thereof.

LC-MS-conditions 02 (if not indicated otherwise): Analytical: Thermo Finnigan MSQ Plus MS with Agilent 1100 Binary Pump and DAD. Column: Zorbax SB-AQ 5 µm, 4.6×50 mm ID from Agilent Technologies. Eluents: A: $H_2O$+0.04% TFA; B: $CH_3CN$; Gradient: 5% B→95% B over 1 min. Flow: 4.50 mL/min. Detection: UV/Vis and/or ELSD, and MS, $t_R$ is given in min.

LC-MS-conditions 07b (if not indicated otherwise): Analytical. Pump: Dionex HPG-3200RS, MS: Thermo MSQ Plus, DAD: Dionex DAD-3000RS, ELSD: Sedere Sedex 85. Column: Zorbax SB-Aq 3.5 µm, 4.6×50 mm ID from Agilent Technologies, thermostated in the Dionex TCC-3200 compartment. Eluents: A: $H_2O$+0.04% TFA; B: $CH_3CN$. Method: Gradient: 5% B→95% B over 1.00 min. Flow: 4.5 mL/min. Detection: UV/Vis and/or ELSD, and MS, $t_R$ is given in min.

HPLC preparative: X-Bridge C18 5 µm, 50×19 mm ID from Waters. Eluents: A: $H_2O$+0.5% $NH_4OH$; B: $CH_3CN$; Gradient: 10% B→90% B over 5 min. Flow: 40.0 mL/min. Detection: UV/Vis and/or ELSD, and MS, $t_R$ is given in min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

Synthesis of Intermediates 1-(p-Tolyl)cyclopropanamine

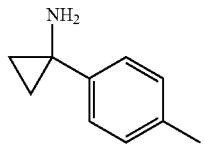

In a flame dried round-bottomed flask equipped with a magnetic stir bar and under inert atmosphere (N$_2$), a solution of p-tolunitrile (1195 mg, 10.00 mmol) in dry Et$_2$O (50 mL) was treated at −78° C. with Ti(Oi-Pr)$_4$ (3.22 mL, 11.00 mmol) followed by EtMgBr (7.33 mL of a 3.0 M solution in Et$_2$O, 22.00 mmol). The resulting yellow suspension was stirred at −78° C. for 10 min, then warmed up to rt. To the resulting black suspension was added BF$_3$.Et$_2$O (2.47 mL, 20.00 mmol) and the reaction mixture was stirred at rt for 1 h. Aqueous 1N HCl (30 mL) was carefully added, followed by Et$_2$O and then 10% aqueous NaOH (100 mL). The layers were separated and the aq. layer extracted with Et$_2$O. The combined org. extracts were dried over MgSO$_4$, filtered and concentrated under reduced pressure. The crude residue was purified by FC (CH$_2$Cl$_2$/MeOH/NH$_4$OH, 1:0:0->90:10:0.5) to get the title amine as a yellow oil. TLC: rf (CH$_2$Cl$_2$/MeOH/NH$_4$OH, 95:5:0.5)=0.46. LC-MS-conditions 07b: $t_R$=0.49 min; [M+H]$^+$=148.29.

Spiro[2.4]hepta-4,6-diene

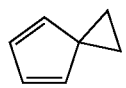

In a flame dried round-bottomed flask equipped with a magnetic stir bar and under inert atmosphere (N$_2$), a mixture of benzyltriethylammonium chloride (18.0 g, 78 mmol) in 50% aqueous NaOH solution (1.2 L) was heated to 45° C. A chilled solution of cyclopentadiene (formed by cracking of cyclopentadiene dimer at 180° C., 140 mL, 1.70 mol) in 1,2-dichloroethane (122 mL, 1.55 mol) was added to the stirred NaOH solution while keeping the internal temperature below 55° C. After completion of the addition (ca. 1.75 h), the reaction mixture was stirred at 50° C. for 2 h and allowed to cool down to rt. The layers were separated, the organic layer washed with 1M NaOH, dried (Na$_2$SO$_4$) and filtered. The crude brown liquid was distilled under reduced pressure (85-95 mbar) and the title compound was obtained as a colorless liquid (bp=45-50° C. at 80 mbar). $^1$H NMR (400 MHz, CDCl$_3$) δ 6.58 (m, 2H), 6.19 (m, 2H), 1.71 (s, 4H).

Diels Alder reaction—formation of (5R,6R)-5,6-bis-[(1-(1S)-ethoxycarbonyl)-ethoxy-carbonyl]-(4S,7R)-[4,7-ethenylene-spiro[2.4]heptane]

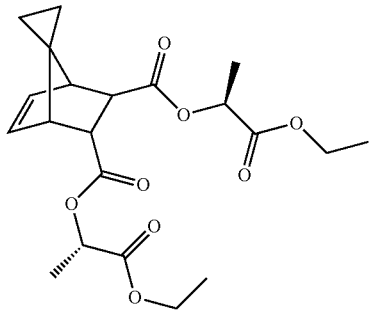 [SMILES: CCOC(=O)[C@H](C)OC(=O)C1C(C(=O)O[C@@H](C)C(=O)OCC)C2C=CC1C21CC1]

In a flame dried round-bottomed flask equipped with a magnetic stir bar and under inert atmosphere (N$_2$), to a solution of (E)-1,2-bis-[((1S)-1-ethoxycarbonylyethoxy-carbonyl]-ethene (7.40 g, 22.69 mmol) in n-hexane (76 mL) was added spiro[2.4]hepta-4,6-diene (3.14 g, 34.04 mmol) at rt. The reaction mixture was stirred at this temperature overnight. The mixture was concentrated under reduced pressure and the crude residue purified by FC (hept/EA, 9:1). The title compound was obtained as a pale yellow oil. TLC: rf (hept/EA, 9:1)=0.25. LC-MS-conditions 02: $t_R$=1.12 min; [M+H]$^+$=409.00. $^1$H NMR (400 MHz, CDCl$_3$) δ 6.44 (dd, J=5.5, 3.0 Hz, 1 H), 6.32 (dd, J=5.5, 2.8 Hz, 1 H), 5.12 (q, J=7.1 Hz, 1 H), 5.06 (q, J=7.1 Hz, 1 H), 4.28-4.14 (m, 4 H), 3.76 (app. t, J=4.0 Hz, 1 H), 2.92 (d, J=4.8 Hz, 1 H), 2.86 (m, 1 H), 2.80 (m, 1 H), 1.55-1.47 (m, 6 H), 1.29 (t, J=7.3 Hz, 3 H), 1.29 (t, J=7.3 Hz, 3 H), 0.70 (m, 1 H), 0.56-0.44 (m, 3 H).

Saponification—formation of (4S,7R)-[4,7-ethenylene-spiro[2.4]heptane]-(5R,6R)-5,6-bis-carboxylic acid

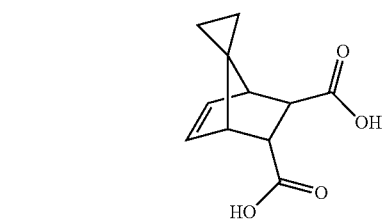 [SMILES: O=C(O)C1C(C(=O)O)C2C=CC1C21CC1]

To a solution of (5R,6R)-5,6-bis-[(1-(1S)-ethoxycarbonyl)-ethoxy-carbonyl]-(4S,7R)-[4,7-ethenylene-spiro[2.4]heptane] (9.51 g, 23.28 mmol) in THF/H$_2$O (1:1, 232 mL) was added LiOH (3.91 g, 93.13 mmol). The reaction mixture was stirred at rt overnight. 1N HCl was added in order to adjust the pH of the reaction mixture to pH=3, the layers separated and the aq. layer extracted with EA (3×). The combined org. extracts were dried over MgSO$_4$, filtered, and concentrated under reduced pressure. The crude residue was purified by FC (CH$_2$Cl$_2$/MeOH, 9:1) to give the title compound as a colorless oil. TLC: rf (CH$_2$Cl$_2$/MeOH, 9:1)=0.31. LC-MS-conditions 02: $t_R$=0.72 min; [M+CH$_3$CN+H]$^+$=250.18.

Iodolactonization—formation of 6-iodo-2-oxohexahydrospiro[3,5-methanocyclopenta[b]furan-4,1'-cyclopropane]-7-carboxylic acid (iodolactone 2)

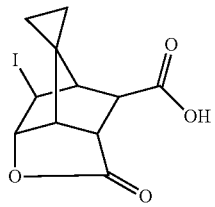 [SMILES: O=C(O)C1C2C(=O)OC3C(I)C1C1(CC1)C32]

To a solution of (4S,7R)-[4,7-ethenylene-spiro[2.4]heptane]-(5R,6R)-5,6-bis-carboxylic acid (5.60 g, 22.32 mmol) in $CH_2Cl_2$ (33 mL) were added $NaHCO_3$ (2.06 g, 24.56 mmol), water (100 mL), KI (1.37 g, 82.60 mmol) and $I_2$ (6.80 g, 26.79 mmol). The reaction mixture was stirred at rt for 3 h. The reaction was quenched by the addition of sat. aq. $Na_2S_2O_3$. The layers were separated and the aq. layer extracted with $CH_2Cl_2$ (3×). The combined org. extracts were dried over $MgSO_4$, filtered, and concentrated under reduced pressure. The crude foam was purified by FC (EA) to give the title compound as a white solid. TLC: rf (EA)= 0.33.

Esterification—formation of methyl 6-iodo-2-oxo-hexahydrospiro[3,5-methanocyclopenta[b]furan-4,1'-cyclopropane]-7-carboxylate

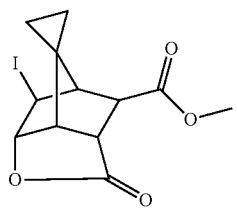 [SMILES: COC(=O)C1C2C(=O)OC3C(I)C1C1(CC1)C32]

In a flame dried round-bottomed flask equipped with a magnetic stir bar and under inert atmosphere ($N_2$), to a solution of enantiopure iodolactone 2 (5.00 g, 14.96 mmol) in dry MeOH (75 mL) was added $TMSCH_2N_2$ (2.0 M in hexanes, 37.0 mL, 74.00 mmol). The reaction mixture was stirred at rt overnight, concentrated under reduced pressure and purified by FC (hept/EA, 4:1) to give the title compound as a white solid. TLC: rf (hept/EA, 4:1)=0.18.

Retro-iodolactonization—formation of (6R)-6-methoxycarbonyl-(4S,7R)-[4,7-ethenylene-spiro[2.4]heptane]-(5R)-5-carboxylic acid

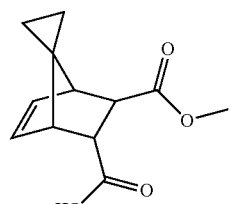

In a flame dried round-bottomed flask equipped with a magnetic stir bar and under inert atmosphere ($N_2$), to a solution of methyl 6-iodo-2-oxohexahydrospiro[3,5-methanocyclopenta[b]furan-4,1'-cyclopropane]-7-carboxylate (2.86 g, 8.21 mmol) in acetic acid (29 mL) was added zinc powder (8.06 g, 123.23 mmol). The reaction mixture was stirred at 65° C. for 4 h, cooled down to rt, filtered and partitioned between water and EA. The layers were separated and the aq. layer extracted with EA (3×). The combined org. extracts were washed with brine, dried over $MgSO_4$, filtered, and concentrated under reduced pressure. The crude residue was purified by FC (hept/EA, 1:1) and the title compound was obtained as a colorless oil. TLC: rf (hept/EA, 1:1)=0.41.

Double bond reduction—formation of (6R)-6-methoxycarbonyl-(4S,7R)-[4,7-ethylene-spiro[2.4]heptane]-(5R)-5-carboxylic acid (WO2010/134014)

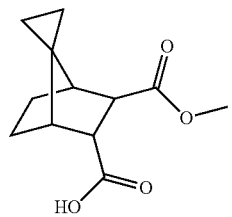 [SMILES: COC(=O)C1C(C(=O)O)C2CCC1C21CC1]

In a flame dried round-bottomed flask equipped with a magnetic stir bar and under inert atmosphere ($N_2$), a deoxygenated suspension of (6R)-6-methoxycarbonyl-(4S,7R)-[4,7-ethenylene-spiro[2.4]heptane]-(5R)-5-carboxylic acid (220 mg, 0.99 mmol), Pd/C 10% (44 mg) and cyclohexene (0.20 mL, 1.98 mmol) in dry THF (2.5 mL) was stirred at reflux for 2 h. The reaction mixture was filtered through celite and the filter cake washed with THF. The filtrate was concentrated under reduced pressure and the title compound obtained as a white solid. TLC: rf (hept/EA, 2:3)=0.48.

Amide coupling with 1-(p-tolyl)cyclopropan-amine—formation of (5R)—$N^5$-(1-(p-tolyl)cyclopropyl)-(6R)-6-methoxycarbonyl-(4S,7R)-[4,7-ethylene-spiro[2.4]heptane]-(5R)-5-carboxamide

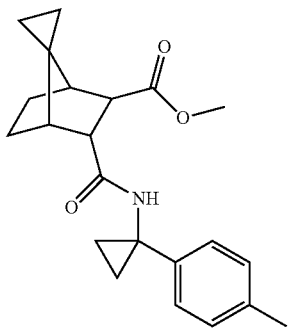 [SMILES: COC(=O)C1C(C(=O)NC2(c3ccc(C)cc3)CC2)C2CCC1C21CC1]

In a flame dried round-bottomed flask equipped with a magnetic stir bar and under inert atmosphere ($N_2$), to a solution of (6R)-6-methoxycarbonyl-(4S,7R)-[4,7-ethylene-spiro[2.4]heptane]-(5R)-5-carboxylic acid (1565 mg, 6.98 mmol) in dry $CH_2Cl_2$ (24 mL) were added a few drops of DMF and oxalyl chloride (0.74 mL, 8.38 mmol). The reaction mixture was stirred at rt for 30 minutes, concentrated under reduced pressure and the residue dried under high vacuum. To a stirred suspension of 1-(p-tolyl)cyclopropanamine (1028 mg, 6.98 mmol) in pyridine (1.68 mL, 20.94 mmol) was added a solution of the above acyl chloride in dry acetone (24 mL). The reaction mixture was stirred at rt for 45 min, diluted with EA and successively washed with aq. 1N HCl, sat. aq. NaHCO$_3$ and brine. The org. layer was dried over MgSO$_4$, filtered, and concentrated under reduced pressure. The crude residue was purified by FC (hept/EA, 1:0->3:1) and the title compound obtained as a yellow solid. LC-MS-conditions 07b: $t_R$=0.93 min; [M+H]$^+$=353.82.

Saponification—formation of (5R)—N$^5$-(1-(p-tolyl)cyclopropyl)-(6R)-6-hydroxycarbonyl-(4S,7R)-[4,7-ethylene-spiro[2.4]heptane]-5-carboxamide

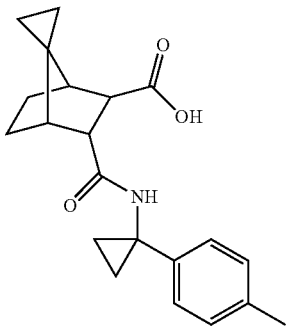 [SMILES: Cc1ccc(C2(NC(=O)C3C(C(=O)O)C4CCC3C43CC3)CC2)cc1]

To a solution of (5R)—N$^5$-(1-(p-tolypcyclopropyl)-(6R)-6-methoxycarbonyl-(4S,7R)-[4,7-ethylene-spiro[2.4]heptane]-5-carboxamide (1540 mg, 4.36 mmol) in THF (23 mL) was added aq. 2N NaOH (12 mL, 24.00 mmol). The reaction mixture was stirred at rt until completion of the reaction. The mixture was then washed with Et$_2$O, the aq. layer acidified and extracted with EA (3×). The combined org. extracts were washed with brine, dried over MgSO$_4$, filtered, and concentrated under reduced pressure to give the title compound as a pale yellow solid. LC-MS-conditions 07b: $t_R$=0.84 min; [M+H]$^+$=340.46.

Preparation of Example

Amide coupling with 2-(4-methylpiperazin-1-yl)ethanamine—formation of (5R)—N$^5$-(1-(p-tolyl)cyclopropyl)-(6R)—N$^6$-(2-(4-methylpiperazin-1-yl)ethyl)-(4S,7R)-[4,7-ethylene-spiro[2.4]heptane]-5,6-dicarboxamide

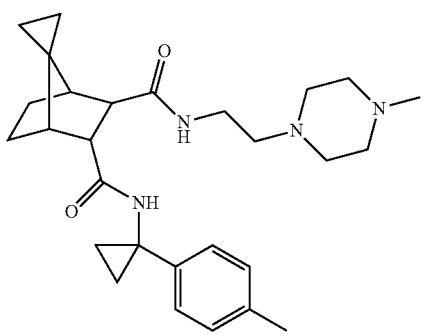 [SMILES: Cc1ccc(C2(NC(=O)C3C(C(=O)NCCN4CCN(C)CC4)C4CCC3C43CC3)CC2)cc1]

In a flame dried round-bottomed flask equipped with a magnetic stir bar and under inert atmosphere (N$_2$), to (5R)—N$^5$-(1-(p-tolypcyclopropyl)-(6R)-6-hydroxycarbonyl-(4S,7R)-[4,7-ethylene-spiro[2.4]heptane]-5-carboxamide (34 mg, 0.10 mmol) in CH$_2$Cl$_2$ (2 mL) were successively added 2-(4-methylpiperazin-1-yl)ethanamine (29 mg, 0.20 mmol), EDC.HCl (39 mg, 0.20 mmol), HOBt (19 mg, 0.12 mmol) and DIPEA (0.09 mL, 0.50 mmol). The reaction mixture was stirred at rt until completion of the reaction. Water was then added, the layers separated and the org. layer dried over MgSO$_4$, filtered and concentrated under reduced pressure. The crude residue was purified by preparative HPLC to get the title compound as a white solid. TLC: rf (CH$_2$Cl$_2$/MeOH/NH$_4$OH, 95:5:0.5)=0.10. LC-MS-conditions 07b: $t_R$=0.63 min; [M+H]$^+$=465.43.

II. Biological Assays

In Vitro Assay

The ALX receptor agonistic activity of the compounds of formula (I) is determined in accordance with the following experimental method.

Experimental Method:

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1'000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% CO$_2$ in AB supplemented with 1 µM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50'000 cells in 70 µl per well and sedimented by centrifugation at 1'000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 µl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the ALX receptor (EC$_{50}$ values, median of n replications) of exemplified compounds are displayed in Table 1.

TABLE 1

| Compound | EC$_{50}$ [nM] |
| --- | --- |
| Example 1: (5R)-N$^5$-(1-(p-tolyl)cyclopropyl)-(6R)-N$^6$-(2-(4-methylpiperazin-1-yl)ethyl)-(4S,7R)-[4,7-ethylene-spiro[2.4]heptane]-5,6-dicarboxamide | 9.4 (n = 17) |

Dansyl-Glutathione Trapping Assay
In Vitro Incubation

Test compounds are generally preincubated at 10 µM in 0.1 M potassium phosphate buffer (pH 7.4) with 1 mg/mL human liver microsomes and 1 mM dansyl-GSH for 5 min at 37° C. in light protected tubes. The reaction is initiated by adding an NADPH-regenerating system. After 60 min, the reaction is stopped by the addition of two volumes of ice-cold methanol with 5 mM dithiothreitol (DTT). Following centrifugation, supernatants are further analysed by HPLC with fluorescence detection. Control experiments are done in the presence of GSH instead of dansyl-GSH in order to identify fluorescent parents and/or metabolites as interference. Another control is performed in the absence of parent drug to determine background signals due to degradation/impurities of dansyl-glutathione.

Analytics/Quantification

Supernatants of incubated samples are introduced into a Shimadzu HPLC system with fluorescence detector ($\lambda_{ex}$ 340, $\lambda_{em}$ 525 nm) capable to run with higher pressure (600 bar). The separation is accomplished using a 4.6×100 mm RP Kinetics column (Phenomenex, 2.6 µm) at 1.5 ml/min. A full gradient is used with water and acetonitrile both acidified with 0.1% formic acid. A volume of 2 ml acetonitrile is added post-column to reduce solvent dependant fluorescence. Dansyl-GSH trapped compounds are identified via visual comparison of chromatograms of incubations and control samples. The amount of trapped material is quantified by an external calibration with known concentrations of dansyl-GSH and expressed in pmol/mg*h. For example 1, the amount of trapped material was less than 100 pmol/mg*h.

Plasma Stability Assay

Rat or human serum adjusted at pH 7.4 with lactic acid or ammonium hydroxide, were equilibrated at 37° C. under orbital shaking in an incubator containing 5% CO2. The reaction was initiated by the addition of 1 µM of compounds (1.5 µl of 1 mM stock solution in DMSO in 1498.5 µl of plasma). At 0.01, 0.25, 0.5, 1, 2, 3, 4 and 6 h, aliquots (100 µl) were transferred in a 96 well plate containing 300 µl MeOH placed on ice to stop the reaction. After vortexing for 20 min at 1400 rpm on an Eppendorf thermomixer, the plates were centrifuged at 3220 g for 20 min at 4° C. and the supernatants were analyzed with LC-MS/MS. Calibration samples in plasma containing 0.1% of dichlorvos were prepared and analysed in parallel to the incubation samples to allow the quantification. Half lives ($T_{1/2}$) in hours were then calculated. In addition the remaining concentration of the respective compound after time $T_{last}$ relative to the concentration at the beginning has been determined (table 2).

TABLE 2 stability in serum

| compound | number of replicates | species | $T_{1/2}$ [h] | $T_{last}$ [h] | remaining concentration at $T_{last}$ [%] |
|---|---|---|---|---|---|
| example 1 | 1 | human | >6 | 6 | 82 |
| example 1 | 1 | rat | >6 | 6 | 100 |

The invention claimed is:

1. A compound of formula (I), wherein the compound is (5R)—N$^5$-(1-(p-tolyl) cyclopropyl)-(6R)—N$^6$-(2-(4-methylpiperazin-1-yl)ethyl)-(4S,7R)- [4,7-ethylene-spiro [2.4] heptane]-5,6-dicarboxamide;

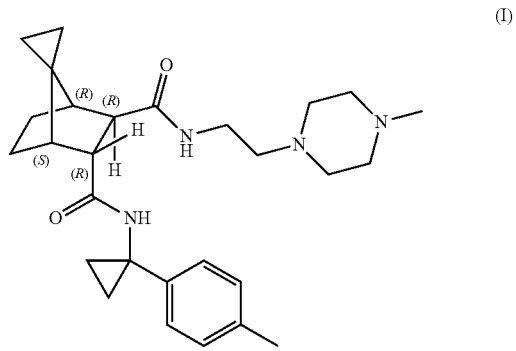

or a salt of the compound.

2. The compound of formula (I) according to claim 1, or a pharmaceutically acceptable salt thereof, wherein the compound or salt thereof is formulated as a medicament.

3. A pharmaceutical composition comprising the compound of formula (I) according to claim 1, or a pharmaceutically acceptable salt thereof, and at least one therapeutically inert excipient.

4. A method of treating a disease comprising administering to a subject in need thereof the compound of formula (I) according to claim 1, -wherein the disease is rheumatoid arthritis, acute lung injury, asthma, cystic fibrosis, inflammatory bowel disease, keratoconjunctivitis sicca, HIV mediated retroviral infections, atopic dermatitis, pulmonary fibrosis or Alzheimer's disease.

5. A method of treating a disease comprising administering to a subject in need thereof the pharmaceutical composition of claim 3, wherein the disease is rheumatoid arthritis, acute lung injury, asthma, cystic fibrosis, inflammatory bowel disease, keratoconjunctivitis sicca, HIV-mediated retroviral infections, atopic dermatitis, pulmonary fibrosis or Alzheimer's disease.

* * * * *